US008883422B2

(12) United States Patent
Berthoud

(10) Patent No.: US 8,883,422 B2
(45) Date of Patent: Nov. 11, 2014

(54) AUTHENTICATION METHOD OF DAIRY PRODUCTS

(75) Inventor: Hélène Berthoud, Bienne (CH)

(73) Assignee: Agroscope Liebefeld-Posieux ALP, Bern (CH)

( * ) Notice: Subject to any disclaimer, the term of this patent is extended or adjusted under 35 U.S.C. 154(b) by 6 days.

(21) Appl. No.: 13/499,025

(22) PCT Filed: Oct. 1, 2010

(86) PCT No.: PCT/EP2010/064673

§ 371 (c)(1),
(2), (4) Date: Aug. 30, 2012

(87) PCT Pub. No.: WO2011/039359

PCT Pub. Date: Apr. 7, 2011

(65) Prior Publication Data

US 2012/0329048 A1    Dec. 27, 2012

(30) Foreign Application Priority Data

Oct. 1, 2009  (EP) .................................... 09172008

(51) Int. Cl.
*C12Q 1/68*     (2006.01)
*C12N 1/20*     (2006.01)
*A23C 19/032*   (2006.01)

(52) U.S. Cl.
CPC ............. *C12Q 1/689* (2013.01); *A23Y 2220/29* (2013.01); *C12Q 1/68* (2013.01); *A23Y 2280/15* (2013.01); *A23C 19/0323* (2013.01)
USPC ...................................... 435/6.12; 536/24.33

(58) Field of Classification Search
None
See application file for complete search history.

(56) References Cited

U.S. PATENT DOCUMENTS

| | | | |
|---|---|---|---|
| 4,764,290 | A | 8/1988 | Currey |
| 5,447,844 | A | 9/1995 | Bricker et al. |
| 6,312,958 | B1 | 11/2001 | Meyer et al. |
| 7,803,547 | B2 * | 9/2010 | Ellis et al. ..................... 435/6.15 |
| 2004/0029295 | A1 | 2/2004 | Brogger et al. |
| 2006/0035288 | A1 | 2/2006 | Green et al. |

FOREIGN PATENT DOCUMENTS

| | | |
|---|---|---|
| CN | 101050437 A | 10/2007 |
| EP | 0327163 A2 | 8/1989 |
| WO | 9617954 A1 | 6/1996 |
| WO | 2005100614 A1 | 10/2005 |
| WO | WO 2005100614 A1 * | 10/2005 |
| WO | 2008003811 A1 | 1/2008 |
| WO | 2008022987 A1 | 2/2008 |
| WO | 2009040563 A1 | 4/2009 |

OTHER PUBLICATIONS

Casey et al. (Naturally occurring genetic markers in *Lactobacilli* and their use to verify the authenticity of Swiss Emmental PDO cheese, Dairy Sci. Technol. 88 (2008) 457-466).*
Weiner et al. (Kits and their unique role in molecular biology: a brief retrospective, BioTechniques, vol. 44, No. 5, pp. 701-704, Apr. 2008).*
Stratagene ("Gene Characterization Kits" 1988).*
Callanan et al. (Insertion sequence elements as mediators of strain diversity in *Lactobacillus helveticus*, International Journal of Food Microbiology 120 (2007) 120-123).*
Ehrmann et al. (Characterisation of IS153, an IS3-family Insertion Sequence Isolated from *Lactobacillus sanfranciscensis* and its use for Strain Differentiation, System. Appl. Microbiol. 24, 443-450 (2001)).*
Callanan et al., "Insertion sequence elements as mediators of strain diversity in *Lactobacillus helveticus*," International Journal of Food Microbiology, 2007, pp. 120-123, vol. 120.
Casey et al., "Naturally occurring genetic markers in *Lactobacilli* and their use to verify the authenticity of Swiss Emmental PDO cheese," Dairy Sci. Technol., 2008, pp. 457-466, vol. 88.
Ehrmann et al., "Characterisation of IS153, an IS3-family Insertion Sequence Isolated from *Lactobacillus sanfranciscensis* and its use for Strain Differentiation," System Appl. Microbiol., 2001, pp. 443-450, vol. 24.
Mahillon et al., "Insertion Sequences," Microbiology and Molecular Biology Reviews, Sep. 1998, pp. 725-774, vol. 62, No. 3.
Nicoloff et al., "ISLpl1 Is a Functional IS30-Related Insertion Element in *Lactobacillus plantarum* That is Also Found in Other Lactic Acid Bacteria," Applied and Environmental Microbiology, Oct. 2003, pp. 6032-6040, vol. 69, No. 10.
Nicoloff et al., "Increased Genome Instability in *Escherichia coli* Ion Mutants: Relation to Emergence of Multiple-Antibiotic-Resistant (MAR) Mutants Caused by Insertion Sequence Elements and Large Tandem Genomic Amplifications," Antimicrobial Agents and Chemotherapy, Apr. 2007, pp. 1293-1303, vol. 51, No. 4.
Papadopoulos et al., "Genomic evolution during a 10,000-generation experiment with bacteria," Proc. Natl. Acad. Sci. USA, Mar. 1999, pp. 3807-3812, vol. 96.
Petrovic et al., "Strain typing with ISLpI1 in *Lactobacilli*," FEMS Microbiol Lett, 2006, pp. 1-10, vol. 255.
Pillonel et al., "Geographic authenticity of Swiss Cheeses: selected results for the food control laboratories and perspective for the future," Mitt Lebensm. Hyg., 2004, pp. 503-513, vol. 95.
Polzin et al., "Copy Number and Location of Insertion Sequences ISS1 and IS981 in *Lactococci* and Several Other Lactic Acid Bacteria," J. Dairy Sci., 1993, pp. 1243-1252, vol. 76.
Ricci et al., "Characterization of *Lactobacillus helveticus* strains isolated from cheeses by distribution studies of insertion sequences," International Journal of Food Microbiology, 2006, pp. 112-119, vol. 112.
Saiki et al., "Primer-Directed Enzymatic Amplification of DNA with a Thermostable DNA Polymerase," Science, Jan. 29, 1988, pp. 487-491, vol. 239, No. 4839.
Schneider et al., "Dynamics of insertion sequence elements during experimental evolution of bacteria," Research in Microbiology, 2004, pp. 319-327, vol. 155.
Zhao Runxiang et al. Fermented Dairy Products. China Dairy Industry, 1999, pp. 26-28, vol. 27, No. 6.

* cited by examiner

*Primary Examiner* — Christopher M Babic
*Assistant Examiner* — Aaron Priest
(74) *Attorney, Agent, or Firm* — The Webb Law Firm

(57) ABSTRACT

The present invention relates to a new method of establishing the authenticity and origin of dairy products, more specifically to the use of lactic acid bacterial strains having strain-specific insertion sequence elements as tools for marking dairy products (such as cheese) and identification thereof. The invention also extends to new lactic acid bacterial strains, their use in the production of dairy products as well as the dairy products containing these bacterial strains.

9 Claims, No Drawings

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial
<220> FEATURE:
<223> OTHER INFORMATION: synthetic oligonucleotide

<400> SEQUENCE: 1
aggctgcttg cgtatc                                                      16

<210> SEQ ID NO 2
<211> LENGTH: 22
<212> TYPE: DNA
<213> ORGANISM: Artificial
<220> FEATURE:
<223> OTHER INFORMATION: synthetic oligonucleotide

<400> SEQUENCE: 2
atcgtcgaac gccgcaagaa ac                                               22

<210> SEQ ID NO 3
<211> LENGTH: 20
<212> TYPE: DNA
<213> ORGANISM: Artificial
<220> FEATURE:
<223> OTHER INFORMATION: synthetic oligonucleotide

<400> SEQUENCE: 3
cgttcggaat aggttatact                                                  20
```

```
<210> SEQ ID NO 4
<211> LENGTH: 21
<212> TYPE: DNA
<213> ORGANISM: Artificial
<220> FEATURE:
<223> OTHER INFORMATION: synthetic oligonucleotide

<400> SEQUENCE: 4
ggtgcaactc tcttcctcga a                                              21

<210> SEQ ID NO 5
<211> LENGTH: 18
<212> TYPE: DNA
<213> ORGANISM: Artificial
<220> FEATURE:
<223> OTHER INFORMATION: synthetic oligonucleotide

<400> SEQUENCE: 5
ggaagggcaa gcaggatt                                                  18

<210> SEQ ID NO 6
<211> LENGTH: 25
<212> TYPE: DNA
<213> ORGANISM: Artificial
<220> FEATURE:
<223> OTHER INFORMATION: synthetic oligonucleotide

<400> SEQUENCE: 6
cttaaactac aagactccag aagaa                                          25

<210> SEQ ID NO 7
<211> LENGTH: 23
<212> TYPE: DNA
<213> ORGANISM: Artificial
<220> FEATURE:
<223> OTHER INFORMATION: synthetic oligonucleotide

<400> SEQUENCE: 7
ggcatcaatt tatagacgcc aat                                            23
```

AUTHENTICATION METHOD OF DAIRY PRODUCTS

The Sequence Listing associated with this application is filed in electronic format via EFS-Web and is hereby incorporated by reference into the specification in its entirety. The name of the text file containing the Sequence Listing is 0115_120993_ST25.txt. The size of the text file is 1,672 Bytes, and the text file was created on Aug. 22, 2012.

FIELD OF THE INVENTION

The present invention relates to a new method of establishing the authenticity and origin of dairy products, more specifically to the use of lactic acid bacterial strains having uniquely located insertion sequence elements as tools for marking dairy products (such as cheese) and identification thereof. The invention also extends to new isolates of lactic acid bacterial, their use in the production of dairy products as well as the dairy products containing these bacterial strains.

BACKGROUND

Protection of valuable goods, products and brands has always been a key requirement of today's markets. In view of a steady increase in counterfeiting and unauthorized distribution of food products there is a need for efficient solutions for products and goods authentication. The ingredients of a counterfeit product may be different from but may also be the same as those of the genuine product (but in adulterated form or of inferior quality), which renders differentiation difficult.

Existing efforts to authenticate products include for example the addition of exogeneous small molecule markers, such as vitamins (e.g. US 2006/0035288), saccharides (e.g. WO 2008/002987), visually detectable markers e.g. by fluorescence, using dyes (e.g. U.S. Pat. No. 6,312,958, US 2004/0029295, EP 0 327 163, U.S. Pat. No. 4,764,290), tracers based on nitrogen- and/or sulphur-containing heterocycles (e.g. WO 2009/040563), or nucleic acids (e.g. WO 96/17954). Other approaches include the identification of geographically dependent indicators (e.g. distribution of isotopes) and indicators influenced by processing (e.g. copper content) (Pillonel et al, Mitt. Lebensm. Hyg. 95, 503 (2004) and references therein), or the identification of genetic markers using PCR-methods, such as genetically mobile elements including insertion sequence elements (or IS elements).

Bacterial IS elements were discovered during early investigations of gene expression in *Escherichia coli* and the bacteriophage lambda. They range from 800 to 2'500 bp in length and can be found in the genome of many different bacteria at numbers varying between a few and a few hundred copies per genome.

The structure of IS elements is typically characterized by the presence of inverted repeat sequences at their terminals and a gene coding for a transposase. They are capable of inserting at multiple sites in the genome or into plasmids (Mahillon et al. 1998). IS have been shown to promote the evolutionary adaptation of hosts (Nicoloff et al. 2003 et 2007, Papadopoulos et al. 1999, Schneider et al. 2004). However, various IS elements have shown different transpositional activities (Papadopoulos et al. 1999, Polzin et al. 1993). The restriction fragment length polymorphism associated with the presence of multiple IS elements proved to be suitable for strain typing of lactic acid bacteria at the infraspecies level (Petrovic et al. 2006, Ricci et al. 2006).

Applicants have discovered that highly variable IS elements that occur at unique locations in a single lactic acid bacterial strains may be used as strain-specific markers for the marking of dairy products as a rapid and efficient tool for their authentication.

SUMMARY OF THE INVENTION

Accordingly, the present invention relates in general to a new method of establishing the authenticity and origin of dairy products and more specifically to the use of lactic acid bacterial strains having uniquely located IS elements as tools for marking dairy products for their identification.

Thus, the present invention relates in a first aspect to a method for identifying the presence or absence of a lactic acid bacterial strain comprising a uniquely located IS elements in a dairy product, comprising detecting the presence or absence of said IS element at a particular locus on the genome.

More specifically, the method of the invention comprises the steps of (a) obtaining a nucleic sample from a dairy product, (b) providing a primer pair specific for a region of said uniquely located IS element and a region of a nucleic acid sequence adjacent to said uniquely located IS element, (c) performing a PCR amplification reaction with said primer pair of step (b) under conditions suitable to produce an amplification product when said uniquely located IS element is present in said nucleic acid sample, and (d) identifying the presence or absence of a lactic acid bacterial strain by detecting the presence or absence of said amplification product.

In specific embodiments the lactic acid bacterial strain comprising a uniquely located IS element, hereinafter also called marker strain (of the invention), is selected from the group consisting of *Pediococcus, Lactobacillus, Streptococcus thermophilus*, preferably *Pediococcus*, such as the one deposited on Sep. 25, 2009 at the Deutsche Sammlung von Mikroorganismen und Zellkulturen GmbH (DSMZ) under accession number DSM 22981, and *Lactobacillus delbrueckii* subsp. *lactis*, such as the one deposited on Sep. 28, 2010 at the Deutsche Sammlung von Mikroorganismen und Zellkulturen GmbH (DSMZ) under accession number DSM 24025.

In a further aspect, the invention also relates to specific primer pairs suitable for use in the methods of the invention, each consisting of a first and a second primer of between 10 and 100, preferably 18 and 35 nucleotides in length, that are sufficiently specific for a fragment of an IS element present in a particular lactic acid bacterial strain as defined above and a fragment of the sequence adjacent to said IS element, respectively, to allow PCR amplification.

In a further aspect, the invention is also directed towards the use of such primers or primer pairs of the invention.

In yet a further aspect the present invention also relates to new isolates of lactic acid bacteria, such as *Pediococcus acidilactici* represented by the isolate deposited with the Deutsche Sammlung von Mikroorganismen und Zellkulturen GmbH (DSMZ) under accession number DSM 22981, and *Lactobacillus delbrueckii* subsp. *lactis* represented by the isolate deposited on Sep. 28, 2010 with the Deutsche Sammlung von Mikroorganismen und Zellkulturen GmbH (DSMZ) under accession number DSM 24025 Included are a mutant or variant thereof, or a bacterium having at least 93 percent 16S rRNA sequence similarity to each of the above strains (hereinafter also called (lactic acid) bacterial strains of the invention).

In a further aspect, the invention also relates to a dairy product, preferably cheese, comprising a lactic acid bacterial strain of the invention or a combination of lactic acid bacterial strains of the invention.

In a further aspect, the invention also relates to the use of a lactic acid bacterial strain comprising uniquely located IS elements for the identification and proof of origin of a dairy product, wherein the proof of origin is indicated by the presence of said lactic acid bacterial strain.

In a further aspect the present invention also relates to a kit for the specific detection of a lactic acid bacterial strain comprising uniquely located IS elements comprising a primer pair as identified hereinabove, for the identification and proof of origin of a dairy product, wherein the proof of origin is indicated by the presence of said lactic acid bacterial strain.

DETAILED DESCRIPTION OF THE INVENTION

The use of "a" or "an" with respect to strains and IS elements is to be understood to include one or more strains or one or more IS elements. Thus combinations of one lactic acid bacterial strain having one or more marker sequence, two or more lactic acid bacterial strains each having one marker sequence, and two or more lactic acid bacterial strains each having two or more marker sequences are included as well. Specific combinations are discussed in the text.

The expression "variant" or "derivative" of a strain as used herein means a strain which differs from another (related) strain of the invention in a specified or unspecified way but share the same marker sequence. Variants can either occur through spontaneous mutation or be made intentionally by genetic manipulation or conventional means including mutation by ultraviolet light sources, by use of chemicals such as nitrosoguanidine and the like.

The expression "variant" or "derivative" with respect to nucleotide marker sequences includes all nucleotide sequences which differ by substitution, deletion, addition of some nucleotides, but which give a PCR product of a similar size (less than 15% bp difference) with primers of the invention.

The term "primer" refers to a single-stranded oligonucleotide capable of acting as a point of initiation of template-directed DNA synthesis under appropriate conditions (i.e., in the presence of four different nucleoside triphosphates and a DNA polymerase) in an appropriate buffer and at a suitable temperature. The appropriate length of a primer depends on the intended use of the primer but is usually sufficient to provide for hybridization under the desired conditions, and is usually between 18 and 35 nucleotides in length. Short primer molecules generally require cooler temperatures to form sufficiently stable hybrid complexes with the template. A primer need not reflect the exact sequence of the template but must be sufficiently complementary to hybridize with a template. The term "primer site" refers to the area of the target DNA to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified. Primer pairs suitable for the present invention are specifically designed to detect a uniquely located IS element and comprises a first primer hybridizing to a fragment within the IS element and a second primer hybridizing to a fragment which is flanking the IS element. Within the context of the present invention, the sequence spanned by the first and second primer is also referred to as a marker sequence.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association."

The term "substantially complementary" means that a sequence, herein a primer or a probe, need not be exactly complementary to its target sequence; instead, the primer or probe need be only sufficiently complementary to selectively hybridize to its respective strand at the desired annealing site. The skilled artisan will understand that substantially complementary sequences need not hybridize along their entire length. A non-complementary base or multiple bases can be included within the primer or probe, so long as the primer or probe retains sufficient complementarity with its polynucleotide binding site to form a stable duplex therewith.

"Specific hybridization" of primers is the annealing to the complementary sequence forming a double-stranded polynucleotide, that provides an initiation site for primer extension and DNA synthesis.

The term "amplicon" or "amplification product" refers to the product of the amplification reaction generated through the extension of a primer pair of the invention. An amplicon may contain exponentially amplified nucleic acids if both primers utilized hybridize to a target sequence. Alternatively, amplicons may be generated by linear amplification if one of the primers utilized does not hybridize to the target sequence. A preferred amplification method utilizes PCR (see Saiki et al. (1988) Science 239:487-4391). The method utilizes a pair of primers as described above. In conventional PCR the primers are mixed with an appropriate buffer containing $Mg^{2+}$, all four deoxynucleotides (dNTPs), a thermostable DNA polymerase and the target DNA (the template). The mix is then heated to a temperature sufficient to separate the two complementary strands of DNA. The mix is next cooled to a temperature sufficient to allow the primers to specifically anneal to complementary sequences. The temperature of the reaction mixture is then optionally reset to the optimum for the thermostable DNA polymerase to allow DNA synthesis (extension) to proceed. The temperature regimen is then repeated to constitute each amplification cycle. Thus, PCR consists of multiple cycles of DNA melting, annealing and extension. The PCR methods used in the methods of the present invention are carried out using standard methods (see, e.g., McPherson et al., PCR (Basics: From Background to Bench) (2000) Springer Verlag; Dieffenbach and Dveksler (eds) PCR Primer: A Laboratory Manual (1995) Cold Spring Harbor Laboratory Press; Erlich, PCR Technology, Stockton Press, New York, 1989; Innis et al., PCR Protocols: A Guide to Methods and Applications, Academic Press, Harcourt Brace Javanovich, New York, 1990; Barnes, W. M. (1994) Proc Natl Acad Sci USA, 91, 2216-2220). The primers or oligonucleotides used in the methods of the present invention are preferably DNA. Within the context of the present invention, the amplification product or amplicon is obtained by performing a PCR amplification reaction using a primer pair of the invention, thereby amplifying the marker sequence (i.e. the sequence spanned by the first and second primer) and obtaining the corresponding amplification product or amplicon.

As used herein, the term "detecting" used in context of detecting the presence of a target nucleic acid sequence, to indicate the presence of a specific strain in a sample, etc. does not require the method to provide 100% sensitivity and/or 100% specificity. As is well known, "sensitivity" is the probability that an assay is positive, given that a sample has a target nucleic acid sequence, while "specificity" is the probability that an assay is negative, given that the sample does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although specificities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" with respect to a nucleic acid sequence (e.g. a fragment within an IS element or a fragment within the nucleic acid sequence flanking the IS element, which serves as the hybridization site of the primer pair of the invention) refers to a sequence of nucleotide residues of between 15 and 2000 by preferably between 15 and 500, more preferably between 50 and 400, most preferably between 100 and 300 nucleotides in length.

The present invention relates in general to a method of authentication and proof of origin of dairy products by marking the dairy products during production with lactic acid bacterial strains having uniquely located IS elements, hereinafter also called marker strains (of the invention). Screening for these strains having uniquely located IS elements will allow establishing proof of origin of a dairy product.

Thus the present invention is directed to a method for identifying the presence or absence of a lactic acid bacterial strain comprising a uniquely located IS element in a dairy product, comprising detecting the presence or absence of said IS element at a particular locus, wherein its presence identifies the presence of a lactic acid bacterial strain in said dairy product. More specifically, the method comprises the steps of
  (a) obtaining a nucleic sample from a dairy product,
  (b) providing a primer pair specific for a region of said uniquely located IS element and a region of a nucleic acid sequence adjacent to said uniquely located IS element,
  (c) performing a PCR amplification reaction with said primer pair of step (b) under conditions suitable to produce an amplification product when said uniquely located IS element is present in said nucleic acid sample, and
  (d) identifying the presence or absence of a lactic acid bacterial strain by detecting the presence or absence of said amplification product.

In specific embodiments, the lactic acid bacterial strain used in the methods of the invention may be any kind of lactic bacteria present in dairy products or used in the dairy industry, for example *Lactococci* such as *Lactococcus lactis* subsp. *lactis*, *Lactococcus lactis* subsp. *cremoris* and *Lactococcus lactis* subsp. *lactic biovar diacetylactis*; *Pediococci* such as *Pediococcus pentosaceus*, *Pediococcus acidilactici*; *Streptococci* such as *Streptococcus thermophilus*; *Lactobacilli* such as *Lactobacillus delbrueckii* subsp. *bulgaricus*, *Lactobacillus helveticus*, *Lactobacillus casei*, *Lactobacillus delbrueckii* subsp. *lactis*, *Lactobacillus rhamnosus*.

A preferred strain is the one deposited on Sep. 25, 2009 at the Deutsche Sammlung von Mikroorganismen und Zellkulturen GmbH (DSMZ) under accession number DSM 22981.

Another preferred strain is the one deposited on Sep. 28, 2010 at the Deutsche Sammlung von Mikroorganismen und Zellkulturen GmbH (DSMZ) under accession number DSM 24025.

In other specific embodiments the uniquely located IS element is at least 75% identical to an IS element selected from the group consisting of readily available IS elements from lactic acid bacteria *Streptococcus thermophilus*, *Lactobacillus casei*, *Lactobacillus delbrueckii lactis*, *Lactobacillus helveticus*, *Lactococcus lactis*, *Leuconostoc lactis*, *Pediococcus pentosaceus*, *Pediococcus damnosus* and *Lactobacillus rhamnosus* including but not limited to IS30, IS 153, ISS1, IS981, IS1076, ISL1, ISLp11, IS904, and IS946 sequence or portions thereof.

In other embodiments the nucleic acid samples of the dairy product (according to step (a) of the above method) may be extracted by methods known in the art.

The methods of the invention comprise screening for one or more lactic acid bacterial strains each comprising a uniquely located IS element. The screening includes hybridizing a nucleic acid sample with one primer pair of the invention for each strain, allowing amplification to occur and obtaining an amplification product for each strain. In specific embodiments the method of the invention includes screening for one strain or a combination of 2 or 3 strains.

Alternatively, the methods of the invention comprise screening for one lactic acid bacterial strain comprising up to one or more uniquely located IS elements which may be achieved by hybridizing a nucleic acid sample with one primer pair of the invention for each IS element, allowing amplification to occur and obtaining an amplification product for each IS element. In specific embodiments the method of the invention includes screening for 1, 2 or 3 IS elements.

The identification of one or more uniquely located IS elements in a specific strain is achieved by (i) first screening for one or more IS elements in a specific strain using appropriate primers, (ii) subsequent amplification of the DNA between the one or more different IS detected in a specific strain as well as in other strains of the same species using specifically designed primers alone or in different combinations, and (iii) detection of PCR products unique for the specific strain. The identified unique PCR products are sequenced, the primers are designed and strain specificity is assessed.

The nucleic acid samples of the dairy product may be amplified using a primer pair of the invention using various methods known to the skilled artisan. Preferably, PCR is used to amplify nucleic acids of interest. Briefly, two primer sequences are purchased that are complementary to regions on opposite complementary strands as described herein, i.e. a first primer hybridizes to a fragment of a uniquely located IS element and a second primer hybridizes to a fragment of the nucleic acid sequence adjacent to said IS element. An excess of oligonucleotides are added to a reaction mixture along with a DNA polymerase, e.g., Taq polymerase and deoxynucleotide triphosphates.

If the uniquely located IS element is present in a sample, the primers will bind to their complementary sequence within the IS element and its flanking sequence and the polymerase will cause the primers to be extended along the marker sequence by adding on nucleotides. By raising and lowering the temperature of the reaction mixture, the extended primers will dissociate from the marker to form reaction products, excess primers will bind to the target sequence and to the reaction products and the process is repeated, thereby generating exponentially amplification products. Cycling parameters can be varied, depending on the length of the amplification products to be extended. An internal positive amplification control (IPC) can be included in the sample, utilizing specific primers, e.g. to monitor both the DNA extraction and any subsequent amplification.

In a suitable embodiment, real time PCR is performed using any suitable instrument capable of detecting the accumulation of the PCR amplification product. Most commonly, the instrument is capable of detecting fluorescence from one or more fluorescent labels. For example, real time detection on the instrument (e.g. a Rotorgene) monitors fluorescence during each PCR cycle. The threshold cycle, or Ct value, is the cycle at which fluorescence intersects the threshold value. The threshold value is determined by software or manually.

An amplification of a nucleic acid sequence can be detected by any of a number of methods well-known in the art such as gel electrophoresis, capillary electrophoresis or "real-time" detection.

In one embodiment, sequences from two or more fragments of interest are amplified in the same reaction vessel (i.e. "multiplex PCR"). Detection can take place by measuring the end-point of the reaction or in "real time."

For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the Taq-Man® system, Scorpion™ primer system and use of intercalating dyes for double stranded nucleic acid. Useful labels include, for example, fluorescent dyes (e.g., Texas red, FAM, JOE, HEX).

In end-point detection, the amplicon(s) could be detected by first size-separating the amplicons, then detecting the size-separated amplicons. The separation of amplicons of different sizes can be accomplished by, for example, gel electrophoresis or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 11% polyacrylamide gel. The separated nucleic acids can then be stained with a dye such as GelRed and the size of the resulting stained band or bands can be compared to a standard DNA ladder.

Thus in a specific embodiment of the method of the invention the presence of the amplification product is indicated by identifying the size (DNA length) of the amplified sequence, by gel elecrophoresis, by means of labeled primers used for said polymerase chain reaction, which primers are incorporated into the amplified sequences, or by means of a labeled DNA probe for annealing with a unique part of the amplified sequence followed by Southern blot analysis.

In a further aspect the invention is also directed towards a primer pair(s) used for hybridization and amplification according to the methods of the invention, more specifically a primer pair comprising a first primer and a second primer each comprising at least 15 contiguous nucleotides, wherein the first primer is sufficiently specific for a sequence within a uniquely located insertion element, and the second primer sufficiently specific for a sequence within the region flanking the insertion element. Most preferably, the pair of primers comprises a first primer of SEQ ID NO: 1 and a second primer of SEQ ID NO: 2 for identifying the presence or absence of a *Pediococcus* strain in a dairy product, or a sixth primer of SEQ ID NO: 6 and a seventh primer of SEQ ID NO: 7 for identifying the presence or absence of a *Lactobacillus* strain in a dairy product, or a combination thereof.

Thus in a further embodiment, the method for identifying the presence or absence of a *Pediococcus acidilactii* strain in a dairy product comprises the steps of
 (a) obtaining a nucleic sample from a dairy product,
 (b) providing a primer pair specific for a region of ISS1SC (GenBank Accession No X94934), and a region of a nucleic acid sequence adjacent to said uniquely located IS element, preferably a primer pair wherein a first primer of the primer pair comprises the sequence SEQ ID NO:1, and a second primer of the primer pair comprises the sequence SEQ ID NO:2
 (c) performing a PCR amplification reaction with the primer pair of step (b) under conditions suitable to allow for hybridization of the first and second primers to occur, and
 (d) detecting the presence or absence of an amplification product as an indication of the presence or absence of said *Pediococcus* strain.

In yet a further embodiment, the method for identifying the presence or absence of a *Lactobacillus delbrueckii* subsp. *lactis* strain in a dairy product comprises the steps of
 (a) obtaining a nucleic sample from a dairy product,
 (b) providing a primer pair specific for a region of IS30 (GenBank Accession No NC_008529), and a region of a nucleic acid sequence adjacent to said uniquely located IS element, preferably a primer pair wherein a sixth primer of the primer pair comprises the sequence SEQ ID NO: 6 and a seventh primer of the primer pair comprises the sequence SEQ ID NO: 7,
 (c) performing a PCR amplification reaction with the primer pair of step (b) under conditions suitable to allow for hybridization of the sixth and seventh primers to occur, and
 (d) detecting the presence or absence of an amplification product as an indication of the presence or absence of said *Lactobacillus* strain It is understood that in yet a further embodiment the above methods can be combined for identifying the presence or absence of a *Pediococcus* and *Lactobacillus* strain in a dairy product.

In yet a further aspect, the present invention relates to isolated lactic acid bacterial strain, preferably to the isolated lactic acid bacterial strain *Pediococcus acidilactici* represented by the isolate deposited with the Deutsche Sammlung von Mikroorganismen und Zellkulturen GmbH (DSMZ) on Sep. 25, 2009 under accession number DSM 22981, or a mutant or variant thereof, or a bacterium having the same marker sequence as said strains, or the isolated lactic acid bacterial strain *Lactobacillus delbrueckii* subsp. *lactis* represented by the isolate deposited with the Deutsche Sammlung von Mikroorganismen und Zellkulturen GmbH (DSMZ) on Sep. 28, 2010 under accession number DSM 24025, or a mutant or variant thereof, or a bacterium having the same marker sequence as said strains.

The present invention also discloses an isolated, pure culture of the lactic acid bacterial strains having the above-mentioned characteristics. As used herein, the expression "pure culture" indicates that the culture contains a biomass of one single isolate of the lactic acid bacterial strain according to the invention, i. e. a clone originating in principle from one cell.

Such a pure culture may be provided as a liquid cell suspension or as frozen, spray-dried or freeze-dried preparation. Preferably the pure culture is a concentrate of cells obtained by separation of cells e. g. by centrifugation or filtration using conventional techniques.

In yet a further aspect, the present invention relates to a culture composition comprising one of the above defined pure cultures or lactic acid bacterial strains, and a microbiologically acceptable carrier.

The composition may, in accordance with the invention, comprise two or more of the above defined pure cultures or lactic acid bacterial strains and may optionally comprises a further lactic acid bacterial species such as selected from the group consisting of *Lactococcus* species., *Lactobacillus* species, *Leuconostoc* species, *Weissella* species, *Oenococcus* species, *Streptococcus* spp., a *Bifidobacterium* species, a *Propionibacterium* species or a *pediococcus* species other than the ones defined hereinabove.

Preferred combinations of strains include combinations of *Lactobacillus* and/or *Pediococcus* and/or *Streprococcus* species. In useful embodiments, the culture compositions of the invention may be an starter or adjunct non-starter culture, preferably adjunct non-starter culture.

It may be preferred that such a culture composition contains at least one marker strain of the invention at a concentration of 100-1000 cfu/ml milk (for production of cheese). Suitable carrier substances include nutrients such as an assimilable carbohydrate or a nitrogen source, which can be utilised readily by the lactic acid bacterial strain. Typically, such a composition is provided in the form of a frozen or freeze-dried composition. In the latter case, the composition may contain cryoprotective compounds.

Thus in a further aspect, the present invention relates to the use of the above defined lactic acid bacterial strain or a pure culture as a starter culture or an adjunct non-starter culture or inactivated culture in the production of a dairy product, preferably cheese. Thus the present invention is also directed towards a method of producing a dairy product, such as cheese, by adding an effective amount of a lactic acid bacterial strain of the invention or a composition to milk.

A suitable bacterial strain is chosen such that it does not affect the cheese making process and/or that it does not affect the quality of the cheese, and/or that it survives the conditions of the cheese making process and/or that its detection is possible in whole cheese, grated cheese and/or cheese rind to allow for proof of origin of the cheese containing said bacterial strain.

As used herein, the term "milk" means any type of fresh or reconstituted, skimmed, semi-skimmed or whole, pasteurized milk or milk component including e. g. cow's milk, buffalo milk, goat's milk, ewe's milk having a dry matter content of 10 to 20% by weight. The processing of milk to obtain a dairy product such as cheese is carried out using conventional process steps.

Typically, the lactic acid bacterial strain is added to the milk in a concentration of viable cells which is at least $10^3$ CFU/g, preferably in the range of $10^3$ to $10^{13}$ CFU/g, such as in the range of $10^5$ to $10^9$ CFU/g, e. g. in the range of $10^6$ to $10^8$ CFU/g of the milk In a further aspect, the present invention also relates to a dairy product, preferably cheese, comprising a lactic acid bacterial strain of the invention or a pure culture or a culture composition thereof.

Thus the invention is also directed towards the use of a lactic acid bacterial strain of the invention or a pure culture thereof or a culture composition thereof for the identification of a dairy product, preferably cheese, and thus for a method for marking a dairy product for identification and proof of origin comprising adding a lactic acid bacterial strain of the invention or a pure culture thereof or a culture composition thereof to a cheese starter composition.

In a further aspect the invention is also directed towards a kit for the specific detection of a lactic acid bacterial strain of the invention or a pure culture thereof or a culture composition thereof comprising a primer pair specific for a region of a uniquely located IS element within said lactic acid bacterial strain or pure culture or culture composition thereof and a region of a nucleic acid sequence adjacent to said uniquely located IS element. Such a kit may be used for the identification and proof of origin of a dairy product, wherein the proof of origin is indicated by the presence of a lactic acid bacterial strain as defined hereinbefore comprising a primer pair according to invention.

Other advantages and characteristics of the invention will become clearly apparent on reading the following description and non-limitative examples given purely by way of illustration. Various modifications of the invention, in addition to those described herein, will become apparent to those skilled in the art from the foregoing description and are intended to fall within the scope of the claims. The disclosures of the various publications cited herein are incorporated by reference in their entireties to the extent necessary for understanding the present invention.

Examples

Materials: The bacterial strains/cultures used include commercially available strains as well as the *Pediococcus acidilactici* strain deposited on Sep. 25, 2009 and the *Lactobacillus delbrueckii* subsp. *lactis* strain deposited on Sep. 28, 2010 pursuant to, and in satisfaction of, the requirements of the Budapest Treaty on the International Recognition of the Deposit of Microorganisms for the Purposes of Patent Procedure with the Deutsche Sammlung von Mikroorganismen and Zellkulturen GmbH (DSMZ) under Accession No. DSM 22981 and DSM 24025, respectively.

Methods: DNA was extracted from cheese by suspending 10 g of grated cheese in Peptonwater (1% peptone, 0.5% NaCl and 2% sodium citrate) and mixing in a stomacher apparatus at room temperature for 3 min. Ten ml cheese extract were mixed with 50 ml SDS 10% and centrifuged 30 min at 4000×g. The supernatant was discarded except about 1 ml which was transferred with the pellet into a 1.5 ml tube. After centrifugation (5 min 10,000×g) the supernatant was discarded and the pellet was suspended in 950 ml TES (0.1 mol L^-1 Tris-HCl, 10 mmol L^-1 EDTA, 25% w/v saccharose, pH 8.0) and lysozyme. The DNA was isolated with the EZ DNA Tissue Kit (Qiagen) after incubation with proteinase K as described in manufacturer's instructions.

Amplification was carried out with a 25 µL reaction mixture containing 2.5 µL of 10× buffer with 15 mmol·L$^{-1}$ MgCl$_2$ (Applied Biosystems, Foster City, Calif.), 0.5 µL of 10 mmol·L$^{-1}$ dNTPs (Promega Corp., Madison, Wis.), 0.2-25 µL of each primer (100 µmol·L$^{-1}$) (Operon Technologies, Alameda, Calif. or Microsynth Laboratory, Balgach, CH) and 0.2-0.25 µL Taq DNA polymerase (5 U·µL$^{-1}$ AmpliTaq Gold) (Applied Biosystems). Amplification was performed with a GeneAmp PCR. System (Applied Biosystems). Amplification products were separated on a DNA 7500 or DNA 1000 LabChip in an Agilent 2100 Bioanalyser according to the manufacturer's instructions (Agilent Technologies, Palo Alto, Calif.).

Example 1

Development of Strain-Specific PCR

To search for a uniquely located insertion sequence, the DNA segment between the IS was amplified by using combinations of upstream and downstream outward facing primers. They were designed for several different IS from lactic acid bacteria.

(a) *Pediococcus Acidilactici:*

The amplification program included a 10 min initial denaturation step at 95° C.; 35 cycles of 95° C. for 30 s, 54° C. for 30 s, and 72° C. for 8 min; and a 10 min final extension step at 72° C.

As example the primer pair Z32771FOUT (5'-CGTTCG-GAATAGGTTATACT; SEQ ID NO:3) designed on region 9519-10424 of sucrose and raffinose operons from *Pediococcus pentosaceus* (Acc. Number Z32771) and ISS1PpROUT (5'-AGGCTGCTTGCGTATC; SEQ ID NO:1) designed on the transposase gene of ISS1SC from *Streptococcus thermophilus* (Acc. number X94934) showed a 1700 bp PCR product only for the *Pediococcus acidilactici* strain of the invention (Acc Nr. DSM 22981)

This amplicon was sequenced with above mentioned IS outward facing primers and new to primers were designed on the IS neighboring gene sequence. PCR between ISS1PpROUT (SEQ ID NO: 1) and the new designed G27 primer (5'-ATCGTCGAACGCCGCAAGAAAC; SEQ ID NO:2) showed a 220 bp PCR product only for the *Pediococcus acidilactici* strain of the invention (Acc Nr. DSM 22981).

(b) *Lactobacillus Delbrueckii* Subsp. *Lactis*

The amplification program included a 10 min initial denaturation step at 95° C.; 35 cycles of 95° C. for 1 min, 59° C. for 1 min, and 72° C. for 3 min; and a 7 min final extension step at 72° C.

As example the primer pair c355a-3 (5'-GGTG-CAACTCTCTTCCTCGAA; SEQ ID NO:4) designed on the IS30 family transposase of *Lactobacillus delbrueckii* subsp. *bulgaricus* (Acc. Number NC_008529) and c370-3 (5'-GGAAGGGCAAGCAGGATT; SEQ ID NO:5) designed on the transposase gene of *Lactobacillus helveticus* (Acc. number NC_010080) showed a 1210 bp PCR product only for the *Lactobacillus delbrueckii* subsp. *lactis* strain of the invention (Acc Nr. DSM 24025)

This amplicon was sequenced with above mentioned IS outward facing primers and new primers were designed on the IS neighboring gene sequence. PCR between new designed Lb102-F primer (5'-CTTAAACTACAAGACTC-CAGAAGAA; SEQ ID NO:6) on the IS30 family transposase of *Lactobacillus delbrueckii* subsp. *bulgaricus* (Acc. Number NC_008529) and the new designed 19108/2010-17 primer (5'-GGCATCAATTTATAGACGCCAAT; SEQ ID NO:7) showed a 136 bp PCR product only for the *Lactobacillus delbrueckii* subsp. *lactis* strain of the invention (Acc Nr. DSM 24025).

Example 2

Strain-Specificity Testing (a) *Pediococcus Acidilactici*:

The outward facing primers for ISS1SC from *Streptococcus thermophilus* used with primer G27 amplify the marker sequence of the *Pediococcus acidilactici* strain of the invention (Acc Nr. DSM 22981).

To verify the presence of the marker sequence exclusively in the marker strain, 50 related strains and 36 cheeses produced without the marker culture and 20 cheeses produces with the marker culture were subjected to the detection of the marker sequence. Results showed that all strains and all cheeses produced without the marker sequence were negative, but all cheeses produced with the marker culture were positive.

(b) *Lactobacillus Delbrueckii* Subsp. *Lactis*

Likewise more than 50 different strains of *Lactobacillus delbrueckii* subsp. *lactis* were tested. Results showed that as expected all tested strains were negative. Only cheeses produced with the marker culture tested were positive.

The invention claimed is:

1. A method for identifying the presence or absence of a lactic acid bacterial strain comprising a uniquely located insertion sequence (IS) element in a dairy product, the method comprising:
   (a) obtaining a nucleic sample from a dairy product,
   (b) providing a primer pair specific for a region of said uniquely located IS element and a region of a nucleic acid sequence adjacent to said uniquely located IS element, the primer pair selected from the group consisting of:
      (i) forward primer comprising SEQ ID NO: 1 and reverse primer comprising SEQ ID NO: 3;
      (ii) forward primer comprising SEQ ID NO: 1 and reverse primer comprising SEQ ID NO: 2;
      (iii) forward primer comprising SEQ ID NO: 4 and reverse primer comprising SEQ ID NO: 5; or
      (iv) forward primer comprising SEQ ID NO: 6 and reverse primer comprising SEQ ID NO: 7,
      wherein at least one of the primers of said primer pair comprises an attached fluorescent dye;
   (c) performing a PCR amplification reaction with said primer pair of step (b) under conditions suitable to produce an amplification product when said uniquely located IS element is present in said nucleic acid sample, and
   (d) identifying the presence or absence of a lactic acid bacterial strain by detecting the presence or absence of said amplification product, wherein said lactic acid bacterial strain is the *Pediococcus acidilactii* strain deposited on Sep. 25, 2009 with the Deutsche Sammlung von Mikroorganismen und Zellkulturen GmbH (DSMZ) under Accession No. DSM 22981 or the *Lactobacillus delbrueckii* subsp. *lactis* strain deposited on Sep. 28, 2010 with the Deutsche Sammlung von Mikroorganismen und Zellkulturen GmbH (DSMZ) under Accession No. DSM 24025, or a combination thereof.

2. The method according to claim 1, wherein the lactic acid bacterial strain is the *Pediococcus acidilactii* strain deposited on Sep. 25, 2009 with the Deutsche Sammlung von Mikroorganismen and Zellkulturen GmbH (DSMZ) under Accession No. DSM 22981 and said primer pair comprises a first primer of SEQ ID NO: 1 and a second primer of SEQ ID NO: 2.

3. The method according to claim 1, wherein said lactic acid bacterial strain is the *Lactobacillus delbrueckii* subsp. *lactis* strain deposited on Sep. 28, 2010 with the Deutsche Sammlung von Mikroorganismen und Zellkulturen GmbH (DSMZ) under Accession No. DSM 24025 and said primer pair comprises SEQ ID NO: 6 and SEQ ID NO: 7.

4. The method according to claim 1, configured to identify the presence or absence of *Pediococcus acidilactici* in a dairy product, comprising the steps of:

(a) obtaining a nucleic sample from a dairy product,
(b) providing a primer pair with a first primer of SEQ ID NO: 1 and a second primer of SEQ ID NO: 2,
(c) performing a PCR amplification reaction with the primer pair of step (b) under conditions suitable to allow for hybridization of the first and second primers to occur, and
(d) detecting the presence or absence of an amplification product as an indication of the presence or absence of said strain *Pediococcus acidilactici*.

5. The method according to claim 1, configured to identify the presence or absence of *Lactobacillus delbrueckii* subsp. *lactis* in a dairy product, comprising the steps of
(a) obtaining a nucleic sample from a dairy product,
(b) providing a primer pair with SEQ ID NO: 6 and SEQ ID NO: 7,
(c) performing a PCR amplification reaction with the primer pair of step (b) under conditions suitable to allow for hybridization of the sixth and seventh primers to occur, and
(d) detecting the presence or absence of an amplification product as an indication of the presence or absence of said strain *Lactobacillus delbrueckii* subsp. *lactis*.

6. A method of preparing a dairy product comprising adding an effective amount of (i) *Pediococcus acidilactici* represented by the isolate deposited on Sep. 25, 2009 with the Deutsche Sammlung von Mikroorganismen und Zellkulturen GmbH (DSMZ) under accession number DSM 22981, or variant thereof, or a bacterium having at least 93 percent 16S rRNA sequence similarity to the said strain, or a pure culture or culture composition thereof or an effective amount of (ii) *Lactobacillus delbrueckii* subsp. *lactis* represented by the isolate deposited on Sep. 28, 2010 with the Deutsche Sammlung von Mikroorganismen und Zellkulturen GmbH (DSMZ) under accession number DSM 24025, or variant thereof, or a bacterium having at least 93 percent 16S rRNA sequence similarity to said strain, or a pure culture or culture composition thereof, or a combination of (i) and (ii), to milk.

7. A method for marking a dairy product for identification and proof of origin comprising adding: (i) *Pediococcus acidilactici* represented by the isolate deposited on Sep. 25, 2009 with the Deutsche Sammlung von Mikroorganismen und Zellkulturen GmbH (DSMZ) under accession number DSM 22981, or variant thereof, or a bacterium having at least 93 percent 16S rRNA sequence similarity to the said strain, or a pure culture or culture composition thereof or an effective amount of (ii) *Lactobacillus delbrueckii* subsp. *lactis* represented by the isolate deposited on Sep. 28, 2010 with the Deutsche Sammlung von Mikroorganismen und Zellkulturen GmbH (DSMZ) under accession number DSM 24025, or variant thereof, or a bacterium having at least 93 percent 16S rRNA sequence similarity to said strain, or a pure culture or culture composition thereof, or a combination of (i) and (ii) to a cheese starter composition.

8. A kit for the specific detection of i) *Pediococcus acidilactici* represented by the isolate deposited on Sep. 25, 2009 with the Deutsche Sammlung von Mikroorganismen und Zellkulturen GmbH (DSMZ) under accession number DSM 22981, or variant thereof, or a bacterium having at least 93 percent16S rRNA sequence similarity to the said strain, or a pure culture or culture composition thereof or an effective amount of (ii) *Lactobacillus delbrueckii* subsp. *Lactis* represented by the isolate deposited on Sep. 28, 2010 with the Deutsche Sammlung von Mikroorganismen und Zellkulturen GmbH (DSMZ) under accession number DSM 24025, or variant thereof, or a bacterium having at least 93 percent 16S rRNA sequence similarity to said strain, or a pure culture or culture composition thereof, or a combination of (i) and (ii) comprising a primer pair specific for a region of a uniquely located insertion sequence (IS) element within said lactic acid bacterial strain or pure culture or culture composition thereof and a region of a nucleic acid sequence adjacent to said uniquely located IS element, wherein said primer pair is selected from the group consisting of:
(i) forward primer comprising SEQ ID NO: 1 and reverse primer comprising SEQ ID NO: 3;
(ii) forward primer comprising SEQ ID NO: 1 and reverse primer comprising SEQ ID NO: 2;
(iii) forward primer comprising SEQ ID NO: 4 and reverse primer comprising SEQ ID NO: 5; or
(iv) forward primer comprising SEQ ID NO: 6 and reverse primer comprising SEQ ID NO: 7,
wherein at least one of the primers of said primer pair comprises an attached fluorescent dye.

9. The method according to claim 6, wherein the dairy product is cheese.

* * * * *